US011778141B2

(12) United States Patent
Dheedene et al.

(10) Patent No.: US 11,778,141 B2
(45) Date of Patent: Oct. 3, 2023

(54) CONTACTLESS CONFIGURATION OF A VIDEOCONFERENCE IN STERILE ENVIRONMENTS

(71) Applicant: RODS & CONES HOLDING BV, Amsterdam-Duivendrecht (NL)

(72) Inventors: Jan Dheedene, Vosselaar (BE); Bruno Dheedene, Amsterdam (NL)

(73) Assignee: RODS & CONES HOLDING BV, Amsterdam-Duivendrecht (NL)

( * ) Notice: Subject to any disclaimer, the term of this patent is extended or adjusted under 35 U.S.C. 154(b) by 0 days.

(21) Appl. No.: 17/560,200

(22) Filed: Dec. 22, 2021

(65) Prior Publication Data
US 2022/0201249 A1 Jun. 23, 2022

(30) Foreign Application Priority Data
Dec. 22, 2020 (BE) .................................. 2020/5967

(51) Int. Cl.
| | | |
|---|---|---|
| *H04L 12/18* | (2006.01) | |
| *H04N 7/15* | (2006.01) | |
| *H04N 7/14* | (2006.01) | |
| *H04L 65/403* | (2022.01) | |
| *G16H 40/67* | (2018.01) | |

(52) U.S. Cl.
CPC ............ *H04N 7/15* (2013.01); *H04L 12/1822* (2013.01); *H04L 65/4046* (2013.01); *H04N 7/147* (2013.01); *G16H 40/67* (2018.01)

(58) Field of Classification Search
CPC ...... H04N 7/15; H04N 7/147; H04L 12/1822; H04L 65/4046; G16H 40/67

USPC ........................................................ 709/204
See application file for complete search history.

(56) References Cited

U.S. PATENT DOCUMENTS

| | | | | |
|---|---|---|---|---|
| 7,650,291 | B2 * | 1/2010 | Rosenfeld | G16H 40/67 705/2 |
| 8,175,895 | B2 * | 5/2012 | Rosenfeld | A61B 5/002 600/300 |
| 9,407,862 | B1 * | 8/2016 | Jawad | H04L 65/403 |
| 10,169,535 | B2 * | 1/2019 | Mentis | G06F 3/0482 |
| 10,347,374 | B2 * | 7/2019 | Tribble | G16Z 99/00 |
| 10,552,574 | B2 * | 2/2020 | Sweeney | A61B 90/98 |
| 10,649,581 | B1 * | 5/2020 | Smith | G06F 9/4843 |
| 10,758,732 | B1 * | 9/2020 | Heldman | A61B 5/291 |
| 10,778,826 | B1 * | 9/2020 | Wang | G06F 3/167 |
| 11,003,308 | B1 * | 5/2021 | Dryer | G06F 3/0484 |
| 11,069,012 | B2 * | 7/2021 | Shelton, IV | H04L 9/14 |

(Continued)

FOREIGN PATENT DOCUMENTS

| | | | | |
|---|---|---|---|---|
| EP | 3148184 | A1 * | 3/2017 | G06F 3/011 |
| KR | 101763204 | B1 * | 8/2017 | H04N 7/14 |
| WO | WO-2016140775 | A1 * | 9/2016 | G06K 9/00 |

OTHER PUBLICATIONS

Opri, Search Report and Written Opinion for BE Application No. 202005967, dated Aug. 19, 2021 (see x/y/a designations at pp. 2-3).

*Primary Examiner* — Melvin H Pollack
(74) *Attorney, Agent, or Firm* — HODGSON RUSS LLP

(57) ABSTRACT

The present invention relates to an improved method of contactless initiation and control of a videoconference between a user in a sterile environment, wherein in the videoconference output is processed from one or more imaging instruments, and from one or more remote users from a predetermined list of a plurality of remote users.

20 Claims, 2 Drawing Sheets

(56) References Cited

U.S. PATENT DOCUMENTS

| | | | |
|---|---|---|---|
| 11,151,796 B2* | 10/2021 | Holmes | G06T 19/006 |
| 11,228,624 B1* | 1/2022 | Oueslati | H04L 65/1069 |
| 11,238,382 B1* | 2/2022 | Graziano | G06Q 10/1095 |
| 11,257,587 B1* | 2/2022 | D'Angelo | A61B 5/0022 |
| 11,295,309 B2* | 4/2022 | Rakshit | G06F 3/013 |
| 11,334,229 B2* | 5/2022 | Victor | G06F 3/0485 |
| 11,368,497 B1* | 6/2022 | Sathyanarayana Rao | H04L 67/12 |
| 2013/0066647 A1* | 3/2013 | Andrie | G16H 20/40 705/2 |
| 2013/0218137 A1* | 8/2013 | Abovitz | A61B 90/90 606/1 |
| 2014/0085399 A1* | 3/2014 | Modai | H04L 65/403 348/14.01 |
| 2014/0125755 A1* | 5/2014 | Thomas | H04N 7/152 348/14.09 |
| 2014/0244720 A1* | 8/2014 | Knodt | H04L 65/4038 709/203 |
| 2014/0317532 A1* | 10/2014 | Ma | H04N 7/152 715/753 |
| 2016/0085922 A1 | 3/2016 | Sweeney | |
| 2016/0173752 A1* | 6/2016 | Caviedes | H04N 1/00204 348/207.11 |
| 2016/0210411 A1 | 7/2016 | Mentis | |
| 2017/0280098 A1* | 9/2017 | Sethuraman | H04L 12/1827 |
| 2018/0303577 A1* | 10/2018 | Sweeney | G06Q 10/087 |
| 2018/0376107 A1* | 12/2018 | Shibaev | G08B 21/043 |
| 2019/0020853 A1* | 1/2019 | Segal | H04N 7/15 |
| 2019/0206004 A1 | 7/2019 | Shelton, IV et al. | |
| 2019/0289198 A1* | 9/2019 | Bosworth | H04N 5/23219 |
| 2019/0311796 A1* | 10/2019 | Kim-Whitty | G16H 80/00 |
| 2020/0084117 A1* | 3/2020 | Kramar | H04L 41/22 |
| 2020/0106965 A1* | 4/2020 | Malia | G06T 11/00 |
| 2020/0120308 A1* | 4/2020 | McMillan | H04N 7/15 |
| 2020/0197825 A1* | 6/2020 | Bear | H04N 5/445 |
| 2021/0051035 A1* | 2/2021 | Atkins | H04N 7/155 |
| 2022/0021680 A1* | 1/2022 | Roedel | H04L 12/1822 |
| 2022/0021977 A1* | 1/2022 | Carrigan | H04R 5/04 |
| 2022/0124128 A1* | 4/2022 | Port | G06V 20/49 |

* cited by examiner

CONTACTLESS CONFIGURATION OF A VIDEOCONFERENCE IN STERILE ENVIRONMENTS

TECHNICAL FIELD

The invention relates to an improved method for configuring and managing a videoconference with external, remote users in a contactless manner in a sterile environment, wherein output from (imaging) instruments in the sterile environment are incorporated into the videoconference.

PRIOR ART

In medical procedures, and other procedures in a sterile environment (such as certain actions in a clean room and similar situations), increasing emphasis is placed on contactless working, and the persons present should avoid interacting with other objects as much as possible, particularly with their hands, as they must remain sterile in order to perform certain actions at a later time.

In a medical setting, a surgeon must be sterile well before the procedure starts, and then may not interact with anything that is not sterile. However, today's operating rooms contain a large number of medical instruments that can be interacted with, but this jeopardizes sterility.

In addition, medical procedures increasingly involve experts from multiple fields, especially complex procedures. However, it is difficult for all of them to be physically present due to the limited space in an OR, but also because each additional person further jeopardizes sterility, and also makes the preparation for each procedure much more cumbersome and longer.

A solution that is increasingly used is video conferencing, whereby the experts can assist and advise the person (or persons) physically present in the sterile space. In this application, smart glasses or other wearable devices with one or more image sensors are often used, so that the person on site has his hands free, and the remote experts have a similar image to the person on site and can thus better coordinate with each other. It is also advantageous that they can clearly direct the person on site due to the strongly overlapping field of vision between the image sensor (what the remote experts see) and what the person on site sees. However, it remains a problem to configure the videoconference, as this should primarily be done by the person in the sterile environment, who has access to the instrumentation and also has an overview of who is needed during the videoconference.

Outsourcing this task is an option, but this leads to the need for an additional, trained person to do it, and it further leads to the need for this additional person to gain remote access to instruments present in the operating room, in order to integrate them in the videoconference as well as to start up and manage them without being on site to be able to solve any problems directly. For this reason, it is nevertheless opted to assign the configuration and management of the videoconference to the person on site, who is thus severely restricted in freedom of action to respect sterility.

The present invention aims to solve at least some of the above problems, and provides an intuitive, simple method that allows a person to set up a videoconference hands-free to which multiple remote users can be invited, and wherein the videoconference gets visual output from imaging instruments in the sterile environment.

SUMMARY OF THE INVENTION

The invention relates to an improved method for contactless initiation and controlling of a videoconference. This videoconference is held with a user in a sterile environment, wherein the sterile environment contains one or more imaging instruments, and one or more remote users from a predetermined list of a plurality of remote users. This videoconference is set up and supported via a server, the server comprising a user database and an instrument database.

The user database comprises the remote users from the predetermined list and a separate, optically readable representation, preferably a QR code, for each of the remote users from the predetermined list. This list typically includes individuals who can self-register or are registered as having a specific skill in a particular field (e.g., anesthesia, knowledge of particular mechanical systems, etc.), and may preferably also be registered as such, to facilitate being looked up, for example. In a specific example situated in a medical context, this list is a collection of all persons associated with a hospital or hospital group, including the employees, but also colleagues with whom is collaborated in a looser context.

The instrument database also further comprises a plurality of imaging instruments and a separate optically readable representation, preferably a QR code, for each of the imaging instruments.

The user in the sterile environment wears a wearable, hands-free image sensor, preferably provided on the user's head, the image sensor being wirelessly connected to the server.

The method comprises the following steps:
a. providing, in the sterile environment and visually perceptibly, the separate, optically readable representations of at least a subset of the plurality of remote users;
b. providing, in the sterile environment and visually perceptibly, the separate, optically readable representations of the one or more imaging instruments in the sterile environment;
c. the initiation of the videoconference by the user in the sterile environment, preferably by reading in with the image sensor an optically readable representation provided in the sterile environment associated with the videoconference and/or with the user in the sterile space;
d. reading in and processing with the image sensor the optically readable representations of one or more remote users to be invited from the user database to the videoconference, wherein the remote users to be invited are invited to the videoconference;
e. reading in and processing with the image sensor the optically readable representations of one or more imaging instruments to be visualized from the instrument database, wherein the visual output of the one or more imaging instruments to be visualized is shared during the videoconference;
f. joining the videoconference by one or more invited remote users through a connection of an electronic display device of the remote users to the server;
g. the initiation of the videoconference by the user in the sterile environment. The remote users in the videoconference are shown a graphical presentation, comprising several sections, via their screen. In this regard, each of the remote users in the videoconference, the user in the sterile environment and the imaging instruments to be visualized are visualized separately in one of the sections, wherein sections associated with one of the imaging instruments to be visualized display at least the visual output of said instrument.

The remote users who have joined the videoconference gain control over the shared visual output, this control comprising at least manipulating focus and contrast of the shared visual output, visually perceivably annotating the shared visual output in the videoconference.

The above method uses optical identifiers (QR codes and the like), which enable the person in the sterile environment to make hands-free contact with the desired persons or instruments in a videoconference using his hands-free wearable image sensor. In a database, the users or instruments are linked to an optical identifier, and thus the correct entity is invited/included in the videoconference.

It is crucial here that, once the videoconference has been initiated, the remote users gain a substantial part of the control over it, whether or not (partially or fully) shared with the user in the sterile environment, whether or not (partially or fully) taken from that user in the sterile user. This allows them to make optimal use of the videoconferencing capabilities, for example providing additional information, adapting, but above all controlling the visual output from the image sensor of the user in the sterile space.

The most difficult aspect of remote procedures is that the remote users are at the mercy of the actions of the person or persons present, and it is often difficult to direct them. The more precise the operation, the more difficult it becomes due to the highly accurate instructions that are required and must be interpreted and executed correctly.

For remote users it is crucial that they have very good visuals of certain zones or objects in the sterile environment (for example during an operation, the area to be operated on a patient's body, in the wound, etc.). If the remote users can control this visual output themselves and edit what they see (change contrast, adjust brightness, apply certain filters, zoom in, annotate), they gain enormous added value in their interactions, which is unprecedented in the current state of the art.

Using the above method, it becomes possible for a user in a sterile environment to set up a videoconference with remote users, often experts in specific fields, who in this way can access the visual feed of the user in the sterile environment via their image sensor shared in the videoconference, but also to imaging instruments in the sterile environment, which could be, for example, visual output from an X-ray device, echocardiograms, or simply images from other angles. By giving remote users control over this visual output, they have the ability to independently edit or manipulate it to their liking, without needing assistance from the person on site who can stay focused on the medical actions.

DETAILED DESCRIPTION OF THE INVENTION

Figure 1:
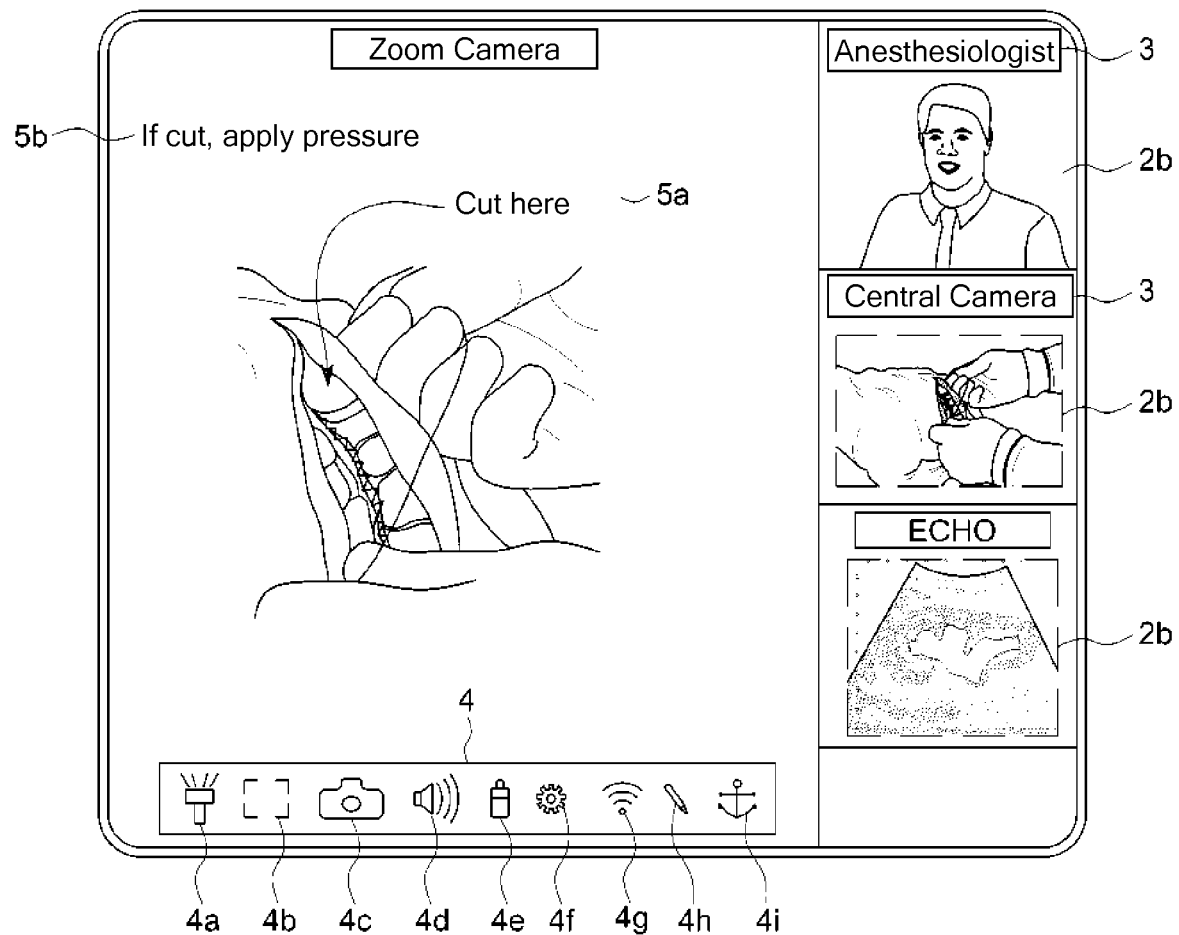
FIG. 1 is a schematic representation of the graphical presentation displayed at a remote user participating in a videoconference, according to an embodiment of the invention.

Unless otherwise defined, all terms used in the description of the invention, including technical and scientific terms, have the meaning as commonly understood by a person skilled in the art to which the invention pertains. For a better understanding of the description of the invention, the following terms are explained explicitly.

In this document, 'a' and 'the' refer to both the singular and the plural, unless the context presupposes otherwise. For example, 'a segment' means one or more segments.

When the term 'around' or 'about' is used in this document with a measurable quantity, a parameter, a duration or moment, and the like, then variations are meant of approx. 20% or less, preferably approx. 10% or less, more preferably approx. 5% or less, even more preferably approx. 1% or less, and even more preferably approx. 0.1% or less than and of the quoted value, insofar as such variations are applicable in the described invention. However, it must be understood that the value of a quantity used where the term 'approximately', 'about' or 'around' is used, is itself specifically disclosed.

The terms 'comprise', 'comprising', 'consist of', 'consisting of', 'provided with', 'have', 'having', 'include', 'including', 'contain', 'containing' are synonyms and are inclusive or open terms that indicate the presence of what follows, and which do not exclude or prevent the presence of other components, characteristics, elements, members, steps, as known from or disclosed in the prior art.

Quoting numerical intervals by endpoints comprises all integers, fractions and/or real numbers between the endpoints, these endpoints included.

In a first aspect, the invention relates to a method according to claim 1. As discussed, this offers the advantage that the user in the sterile environment can start the videoconference hands-free. The startup involves starting a new session, where a number of external users can be invited, and a number of instruments can have their feed added to the videoconference, thereby sharing visual output through the graphical presentation that is visible to the participants. It should be further noted that even with regard to instruments that generate a (visual) output and are not present in the sterile environment, their output can be included in the videoconference. These can be instruments that operate remotely themselves based on output from the sterile environment, due to cost, size, or other circumstances (generation of heat, noise, hazardous radiation, etc.), but whose output can still be relevant in certain procedures.

Once the necessary remote users have been added, the user on site (or possibly a remote user) can initiate the videoconference, whereby control is (partially or fully) transferred to the remote users.

This control comprises at least manipulating focus (zooming in and out), adjusting contrast and annotating the shared visual output. An action by a remote user on one or more of the shared visual outputs becomes visible in the visual presentation of the videoconference shared between the remote users and the user in the sterile environment. In this way, the remote users can pass on feedback and instructions to the user on site in a simple and clear way (as well as share among themselves and continue working on each other's annotations).

Additional functionalities can be transferred to the remote users, which may or may not be partially or completely taken from the user on site, as they can no longer perform manual manipulations with regard to the hands-free image sensor without compromising sterility. By explicitly taking the control away, this limitation can be highlighted more clearly, and the propensity of the user on site to violate it can be reduced.

Additional functionalities may include, but are not limited to, one or more from the following list. Note that some functionalities also depend on the hardware present on the hands-free image sensor and/or instruments in the sterile environment (or even instruments outside the sterile environment whose output is shared in the videoconference).

In a preferred embodiment, the image sensor of the user in the sterile environment is integrated in a hands-free device comprising a display, wherein the user in the sterile environment is shown said graphical presentation via the display. Preferably, this hands-free device is a set of smart glasses or a head-mounted device (HMD) with image sensor(s). The device comprises one or more screens, preferably in the form of a microdisplay such as in smart glasses, or even a (partially transparent) visualization on the glasses.

In a preferred embodiment, the method comprises a step of confirming the videoconference by the user in the sterile space, wherein the confirming initiates the videoconference and wherein the initiation prevents the reading and processing of optically readable representations by the user in the sterile space without prior approval of a remote user. By blocking this functionality, there is no danger during a procedure that the image sensor invites additional participants and/or instruments, for example by accidentally capturing one of the other optically readable codes in the operating room. This can put additional strain on the teleconference, and even potentially cause connectivity issues, but also requires additional processing power from the image sensor, while it is critical that it devote as much capacity as possible to optimizing the connections, and in particular the visual output shared from the image sensor. In addition, this prevents unwanted persons from being invited during a procedure, so that the user has increased freedom of movement on site.

Preferably, one or more of the remote users can once again allow reading and processing in a simple manner, such as an icon provided for this purpose in the graphical presentation of the teleconference.

In a preferred embodiment, each imaging instrument is provided with an electronic unit that can be removably connected. In a preferred embodiment, this is a smartphone or a similar device, most preferably a device with a display. The electronic unit is configured to enable a wired or wireless (preferably wireless, such as Wi-Fi) connection, and is configured to run a connection protocol for joining the imaging instrument to a videoconference. The unit is connected to the imaging instrument, and can access the imaging data thereof. When starting the protocol, the electronic unit will show an optically readable representation (preferably a QR code) that allows the system to identify the electronic unit. When the electronic unit enters the videoconference, it essentially functions as an intermediary for the imaging instrument and forwards the image data from the imaging instrument to the videoconference for display. In doing so, for instance via a smartphone, it allows an easy setup as the electronic unit is pre-configured to run the necessary programs, and is able to wirelessly (or wiredly) forward its data for sharing with the videoconference and its users. This way, even more antiquated imaging instruments can be easily used, as the electronic unit takes over the more modern functions, while just taking the image data from the instrument.

As such, the instrument database comprises a list of the electronic units, and allows the system and method to identify these based on the optically readable representation that was read from the electronic unit. The instrument database thus no longer provides for a fixed link between the imaging instrument and optically readable representation, but provides an exchangeable intermediary in the form of the electronic units, which allows for a fast and easy introduction of new imaging instruments, switching of imaging instruments, and ensured connectivity. In some embodiments, the instrument database is no longer fixed or necessary, and the electronic unit automatically creates a new entry therein by generating an optically readable representation. The method thus comprises the additional steps of connecting the electronic units to the imaging instruments, whereby the electronic units are provided access to the image data thereof. This is for instance easily achieved by connecting the electronic unit to a DVI (digital visual interface) or similar visual interface of the imaging instruments.

In this sense, the method can be redefined as a method for contactless initiation and controlling of a videoconference between a user in a sterile environment comprising one or more imaging instruments, and one or more remote users from a predetermined list of a plurality of remote users, via a server, the server comprising a user database, the user database comprising the remote users of the predetermined list and a separate, optically readable representation, preferably a QR code, for each of the remote users of the predetermined list, the user wearing in the sterile environment a wearable, hands-free image sensor, preferably provided on the user's head, the image sensor being wirelessly connected to the server, the method comprising the following steps:
  a. providing, in the sterile environment and visually perceptibly, the separate, optically readable representations of at least a subset of the plurality of remote users, preferably via an electronic unit with a display, for instance a smartphone;
  b. providing, in the sterile environment and visually perceptibly, the separate, optically readable representations of electronic units connected to the one or more imaging instruments in the sterile environment, the electronic units comprising a display and having access to image data from the imaging instruments, the electronic unit being for instance a smartphone;
  c. the initiation of the videoconference by the user in the sterile environment, preferably by reading in with the image sensor an optically readable representation provided in the sterile environment associated with the videoconference and/or with the user in the sterile space, most preferably said optically readable representation being linked to at least one remote user to join the videoconference;
  d. reading in and processing with the image sensor the optically readable representations of one or more remote users to be invited from the user database for the videoconference, wherein the remote users to be invited are invited to the videoconference, this step in some cases forming part of the previous step;
  e. reading in and processing with the image sensor the optically readable representations of the electronic unit of one or more imaging instruments to be visualize, wherein the visual output of the one or more imaging instruments to be visualized is shared during the videoconference;
  f. joining the videoconference by one or more invited remote users through a connection of an electronic display device of the remote users to the server;
  g. the initiation of the videoconference by the user in the sterile environment;
wherein the remote users in the videoconference are shown via their screen a graphical presentation comprising several sections, wherein each of the remote users in the videoconference, the user in the sterile environment and the imaging instruments to be visualized are visualized separately in one of the sections, and wherein sections associated with one of the imaging instruments to be visualized display at least the visual output of said instrument;
wherein the remote users who have joined the videoconference gain control over the shared visual output, this control comprising at least manipulating focus and contrast of the shared visual output, visually perceivably annotating the shared visual output in the videoconference.

Initiating the session directly by reading in a remote user their representation (QR code or the likes thereof), provides for the advantage that the number of actions is even further reduced, combining the initiation of the session and the introduction of the remote user. Again, this is preferably done by generating a representation digitally that is associated to the remote user, for instance via a smartphone. This way, the person initiating the session can easily ensure he has the correct remote user, for instance by searching for them by name, etc., at which point the associated representation is generated.

Similarly, by providing electronic units for the imaging instruments, they are at the same time provided with an identifier that ensures proper recognition of the correct instrument, and at the same time provide for a component that can ensure reliable transmission of the created image data, for instance by providing a module adapted to connect to Wi-Fi or a similar wireless or wired network. This way, even antiquated imaging instruments can be easily used.

In many embodiments, there will be only one single remote user. In some embodiments, additional spectators may join the videoconference. However, these will not be able to control or affect the feeds from the instruments or other users.

In a preferred embodiment, the image sensor of the user in the sterile room can be controlled by the remote users in the videoconference, and wherein visual output of said image sensor is displayed in the graphical presentation. Controlling the image sensor is not only limited to manipulating its captured images (e.g., adjusting brightness), but also comprises manipulating physical settings of the image sensor, such as one or more of the orientation, physical zoom, adjusting shutter speed when taking of still images, adjusting resolution (increasing or decreasing), adjusting mode (thermal images, etc.). In particular, adjusting the orientation and zoom is of great importance, since accurate control of the user on site by a remote user is very difficult. Allowing remote users to directly control the image sensors greatly simplifies this process.

Alternatively, or additionally, one or more stationary image sensors can also be provided in the space, the orientation of which can be controlled by a remote user, and/or in certain embodiments also mobile image sensors that can be controlled remotely.

In a preferred embodiment, the visual output of at least one of the imaging instruments is a video feed, preferably where the remote users can pause the video feed. In this way, remote users can easily annotate a paused image, or lifting the still image and use it as a separate shared visual output in situations where more perspectives are needed than image sensors are available (or where older images are needed). Finally, this can also be useful for a later analysis of the procedure.

In a preferred embodiment, the remote user can select a section of the graphical presentation as focus, wherein the visual output of the selected section is magnified in the graphical presentation. Preferably, each remote user can do this, or alternatively only a subset of these (who have a higher permission level, and possibly also other privileges, such as freezing images, inviting other remote users, etc.).

The graphic presentation is preferably displayed on screens at the (remote) users, wherein a substantial part of the utilized surface of the screen is provided for the visual output that is focused on, as a focus zone. This can be determined by a (remote) user to be applied to every other user, or only to themselves. The individual sections are displayed conglomerated next to, around, below or to the side of the surface where the visual output is displayed in focus, similar to contemporary teleconferencing such as Zoom®, Skype for Business® and others. By giving remote users the ability to determine where the focus is for each participant in the conversation, it is easier to clearly display what is being discussed. In addition, this is very useful when providing annotations so that they are visible to all.

However, it is most advantageous for the user on site, who has little or no control over the graphical presentation, but through appropriate assistance from the remote users, can see the desired/necessary visual output in the focus zone.

In a preferred embodiment, the method comprises an automated step of periodically adjusting the resolution at which the magnified visual output (focus) of the selected imaging instrument is displayed on the remote users' screen, depending on at least the incoming bitrate of data transfer from the selected imaging instrument. Preferably, the resolution of each of the visual outputs displayed on the graphical presentation is adjusted according to the quality of the connections.

Preferably, the bitrate of the data transfer of the visual output that is not magnified is decreased in order to maximize the bitrate of data transfer of the visual output that is being magnified.

When displaying the graphical presentation, the bitrate of the magnified visual output is measured periodically (e.g., every 30, 15, 10, 5, 2 seconds), and based on this it is determined whether the image quality is too high (or too low), for example by comparison with predetermined limits (lower and upper limit) and is then automatically acted upon by adjusting the image quality accordingly. Determining whether the image quality is too high or too low is preferably done on the basis of a number of past measurements of the bitrate, preferably at least the last 2, more preferably at least the last 5 values thereof. If the bitrate exceeds a predetermined upper limit, the visual output is downloaded at a higher resolution to obtain a higher image quality. If the bitrate falls below a predetermined lower limit, the visual output is downloaded at a lower resolution to obtain a lower image quality.

In a specific preferred scenario, the comparison of the last X measured bitrates against the predetermined upper or lower limit is done as follows: If each of the X bitrates are above the upper limit or below the lower limit, the quality is automatically increased or decreased, respectively.

If all but 1 of the last X bitrates are above the limit, and the one not above is at most 20% below the limit, the quality is increased.

If all but 1 of the last X bitrates are above the limit, and the one not above it is at most 40% below the limit, and the two last measured bitrates are above the limit, the quality is increased.

If all but 2 of the last X bitrates are above the limit, and the 2 not above are at most 20% below the limit, and the last measured bitrate is above the limit, the quality is increased.

Note that variations on the flow above are also considered, such as other deviations for the 'underscoring' bitrates, for example 5%, 10%, 15%, 25%, 30%, 35%, 45%, 50% or intermediate values, or the removal of one or more of the last three conditions. Similar rules can also be drawn up for quality reduction, so that if the bitrate is too low in not all of the last X measured bitrates, this can still lead to a reduction if the 'high' scoring bitrate is only slightly higher than the threshold value (see above).

In a preferred embodiment, the method comprises an automated step of periodically adjusting the resolution at which the visual output of one or more of the imaging instruments is shared via the videoconference, depending on at least the bitrate of data transfer over the connections of the display devices of the remote users.

It should be understood that adjusting the resolution can be performed according to the same rules as described above.

In a preferred embodiment, the wearable image sensor of the user in the sterile environment comprises at least two mutually different image sensors, wherein at least one of the image sensors comprises a zoom lens, and the control by the remote users comprises varying the focal length of the zoom lens. Providing an additional image sensor that allows remote users to adjust the focus distance allows them to exercise greater control over the images shared via the teleconference.

In a preferred embodiment, between start-up and initiation of the videoconference, the user in the sterile environment is authorized to autonomously read in and process optically readable representations of one or more remote users to be invited, and/or to autonomously read in and process optically readable representations of one or more imaging instruments to be visualized from the instrument database. After the initiation of the videoconference, the reading in and processing of optically readable representations by the image sensor of the user in the sterile environment is disabled, and after initiation, the reading in and processing of optically readable representations by the image sensor of the user in the sterile environment can be turned on by one of the remote users who joined the videoconference.

As indicated earlier, after initiating the videoconference, control is taken from the user on site, and almost completely transferred to (one or more of) the remote users. The transferred control then relates in particular to inviting participants (both remote users and instruments) to the videoconference.

The purpose of this is that the user sets up the videoconference completely on site in the preparation phase and then invites the desired participants. Once the videoconference has been started, the focus of the user on site is reserved for performing the procedure, and the remote users can initiate any further actions themselves (such as inviting additional participants) or provide authorization to the user on site to take actions with regard to the videoconference.

In a preferred embodiment, the remote users may provide additional visual output on the graphical presentation. The remote users typically participate in the videoconference via an electronic device with display and input mechanisms, such as touchscreen, keyboard, mouse, joystick and/or others, and can annotate the graphical presentation through the input mechanisms.

On the other hand, the remote users can provide additional visual output, such as by sharing a screen of their PC, laptop or other, sharing a file, and/or via their own image sensor (webcam and the like).

In a preferred embodiment, the instruments whose output is shared in the videoconference share the output via a wireless connection, preferably via Wi-Fi. For this purpose, a WAP or wireless access point is preferably provided in the sterile environment, through which the instruments can share their output via Wi-Fi directly with the participants in the videoconference. This avoids having to route the output of the instruments through a local server.

In a preferred embodiment, the instrument database further comprises a plurality of non-visual output-generating instruments and a separate, optically readable representation, preferably a QR code, for each of the non-visual output-generating instruments, the method further comprising the following step:

reading in and processing with the image sensor the optically readable representations of one or more non-visual output-generating instruments to be visualized from the instrument database, wherein the non-visual output of the one or more non-visual output-generating instruments to be shared is shared during the videoconference in a section associated with the non-visual output-generating instrument.

It should be understood that not all relevant output is visual. For example, auditory input can also be shared (heart monitor) during the videoconference, and for this, corresponding protocols are provided to receive the output of these instruments in the videoconference, which protocols are in line with those for inviting imaging instruments, namely through the reading in of an optically readable representation (QR code).

In a preferred embodiment, the optically readable representation, such as a QR code, is provided on or near the imaging instrument. Preferably, this is provided as close as possible to a screen of the instrument, as this is often an intuitively recognizable part of the instruments.

Alternatively, or additionally, the optical representations can also be provided in a legend in a book, map, panel or on a wall in the sterile space, so that the user can easily read them on site.

In a preferred embodiment, one or more of the imaging instruments further generates non-visual output, the non-visual output being shared during the video conference.

In a preferred embodiment, an imaging instrument is provided in the sterile environment, which is configured to display the graphical presentation of the videoconference. Although the user in the sterile environment preferably also has a portable screen via their hands-free image sensor on which the videoconference is shared (for example, via smart glasses), it is advantageous to provide a dedicated screen that can display the graphical presentation of the videoconference. In certain embodiments, said imaging instrument may be configured to be subordinate to the hands-free device of the user on site, and may, for example, always display only a section that is in focus (and would normally be displayed magnified on the display of the wearable device).

In a preferred embodiment, remote users may provide augmented reality content in the shared visual output for marking objects and/or zones in the visual output, wherein said augmented reality content is anchored to the marked object and/or zone, and wherein upon movement of the marked object and/or zone, the position of the augmented reality content is adjusted based on said movement.

By annotating certain images with augmented reality content (hereinafter referred to as 'annotation'), remote users can choose that these annotations are anchored to a certain position or object in the image (e.g., location of or for an incision), and not be static (i.e., anchored to a particular pixel). The system is hereby configured to store the location/position of the annotation, with all relevant data stored with it. The aim here is that, when the position of the image sensor that captures the annotated image changes, the relative position is maintained, and the annotation therefore moves along as the image moves. This ensures that with less stable image sensors, the annotation retains its desired meaning or purpose.

Adjusting the position of the augmented reality content in the displayed visual output can be achieved in several ways. On the one hand, this can be done by using gyroscopes and similar systems, which can determine the change in orientation/position of the image sensor, and as a result of which the position of the augmented reality content can be recalculated. Alternatively, or additionally, it is also possible to opt for object recognition. By considering the area around it, or even the entire image when placing the annotation, it can be compared with images from new points of view, and the position of the annotation can be updated accordingly.

In particular the combination of the above two can be useful, whereby the object recognition is preferably used to fine-tune the 'slower' recalculation based on determination of adapted orientation/position via gyroscopes and related sensors.

The augmented reality content can take many forms, such as text, characters, a sequence of images, etc. One or more different annotations can be anchored to an object/position, while additionally unanchored annotations can be added (which have a fixed position in the display of the image, e.g., for general comments).

In what follows, the invention is described by way of non-limiting examples illustrating the invention, and which are not intended to and should not be interpreted as limiting the scope of the invention.

EXAMPLES

Example 1

FIG. 1 shows a schematic representation of the graphical presentation visible to a remote user participating in a videoconference.

The graphical presentation (1) is displayed on a screen of an electronic device of the remote user, preferably a laptop, tablet or PC, provided with mouse, joystick, keyboard, touchscreen, or other as input mechanisms. The presentation (1) can optionally be maximized or displayed in a different format on the screen.

The graphical presentation (1) comprises a number of sections (2a, 2b), including a magnified section (2a), and a number of 'regular' sections (2b). Each of the sections (2a, 2b) represents a remote user, which may or may not be displayed visibly via their own image sensor, or an imaging instrument.

In this case, the magnified section (2a) represents the visual output of a zoom lens image sensor on the wearable device of the user on site, as can also be seen in a label (3) in said magnified section (2a). The other sections (2b) are also provided with such labels (3). In the graphical presentation (1) there is an anesthesiologist present, visible in the label (3) of the top section (2b), and the visual output of a central camera on the hands-free device of the user on site. Finally, the visual output of an ultrasound device is also available through the videoconference in the lower section (2b).

The remote user (anesthesiologist in this case) can choose as desired which visual output to visualize in the magnified section (2a), for example by touch interaction with the section displaying the visual output of the central camera.

Also provided on the graphical presentation (1) is an action toolbar (4) for controlling or manipulating the shared visual output, in particular that in the magnified section (2a). This is often made possible via icons (4a-4g) in the toolbar, which can be set according to the wishes of the users.

In this case, the toolbar (4) has the option to control a lamp (4a) on the image sensor of the user on site, they can maximize the graphic presentation in their screen (4b), they can take a photo (4c) of the image in the magnified section (2a), the videoconference sound level can be adjusted (4d), the battery life of the image sensor of the user on site is displayed (4e), settings can be changed (4f), the connection strength can also be displayed (4g), and finally annotations can be provided, both static (4h) and anchored (4i). It should of course be appreciated that the foregoing is only an example, and that additional functionalities can be provided, such as adjusting contrast, zooming in, adjusting the orientation of the image sensor, etc.

Finally, the magnified section (2a) has two forms of annotation, one anchored (5a), which will move along with the area on which it is depicted, the other stationary (5b), which will remain substantially in the same position in the magnified section (2a).

Example 2

Figure 2:
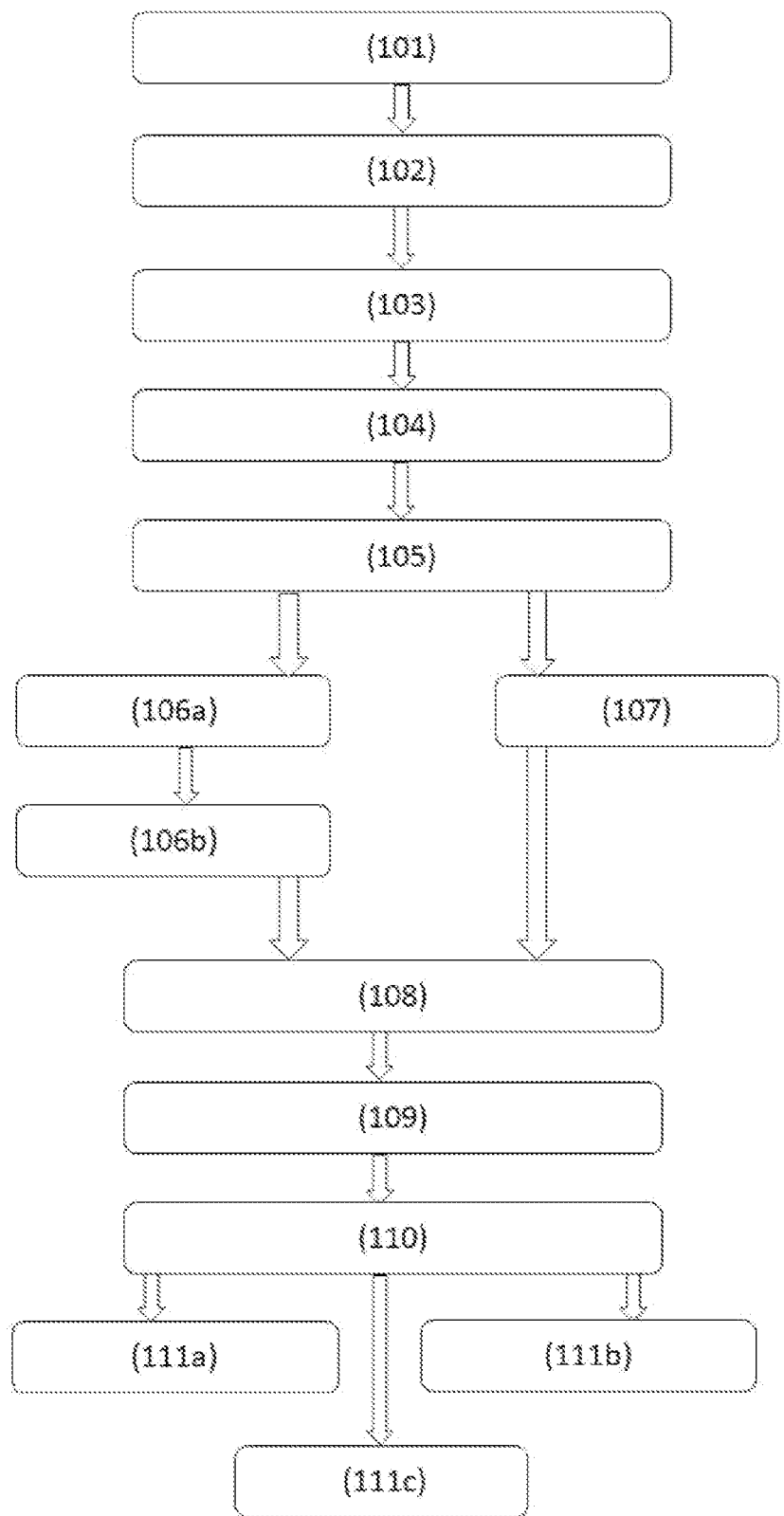
FIG. 2 shows a process flow around setting up and conducting a videoconference according to an embodiment of the invention.

FIG. 2 depicts a process flow (100) of setting up a videoconference according to an embodiment of the present invention in the context of a hospital, and in particular an operation.

In a first step (101) a preparing person (possibly the user on site, but often nursing staff) ensures that the necessary optically readable presentations are provided on the instruments in the operating room, as well as for the participants in the videoconference, possibly using a 'directory' containing all operators associated with the hospital. This action can be performed well in advance, as it can also be used in the further future and later procedures.

Prior to the medical procedure, the user on site ensures that they are sterile (102), whereupon they can enter the sterile space, and then via an HMD (head-mounted display) device with image sensor captures some of the optically readable representations (103) and these are processed (104). When processed, they are automatically linked to the corresponding remote user or instrument from the user database or instrument database (105), and these are either invited to participate in the videoconference (106a), or the visual output of the instrument is automatically acquired and shared via the videoconference (107). When inviting remote users, they must accept the invitation, and they can access the videoconference on an electronic device with a display (106b) either via a specific program or via a web page, preferably by logging into their account.

All invited users and 'invited' instruments are visually represented in a graphical presentation of the videoconference (108).

Once the user on site has invited all remote users and instruments to the videoconference, they initiate the videoconference (109), and control of the videoconference is partially transferred to the remote users (110), who can then select and magnify certain sections (111a), invite additional instruments and/or remote users (111b), manipulate the image displayed in the magnified section, such as, for example, change contrast, zoom in, annotate, etc. (111c).

The present invention should not be construed as being limited to the embodiments described above and certain modifications or changes may be added to the examples described without having to re-evaluate the appended claims. For example, the present invention has been described with reference to medical procedures, but it should be understood that the invention can be applied to, for example, hazardous operations, such as explosives dismantling or maintenance in high radioactivity environments, maintenance of deep-sea systems, hard-to-access systems or equipment, and others. In any of these situations, the expertise of several people would be extremely beneficial, but it is either impossible or too high an additional risk.

The invention claimed is:

1. A method for contactless initiation and controlling of a videoconference between a user in a sterile environment comprising one or more imaging instruments, and one or more remote users from a predetermined list of a plurality of remote users, via a server, the server comprising a user database and an instrument database, the user database comprising the remote users of the predetermined list and a separate, optically readable representation for each of the remote users of the predetermined list, the instrument database comprising a plurality of imaging instruments and a separate, optically readable representation for each of the imaging instruments, the user wearing in the sterile environment a wearable, hands-free image sensor, the image sensor being wirelessly connected to the server, the method comprising the following steps:

providing, in the sterile environment and visually perceptibly, the separate, optically readable representations of at least a subset of the plurality of remote users;

providing, in the sterile environment and visually perceptibly, the separate, optically readable representations of the one or more imaging instruments in the sterile environment;

the initiation of the videoconference by the user in the sterile environment;

reading in and processing with the image sensor the optically readable representations of one or more remote users to be invited from the user database for the videoconference, wherein the remote users to be invited are invited to the videoconference;

reading in and processing with the image sensor the optically readable representations of one or more imaging instruments to be visualized from the instrument database, wherein the visual output of the one or more imaging instruments to be visualized is shared during the videoconference;

joining the videoconference by one or more invited remote users through a connection of an electronic display device of the remote users to the server;

confirming the videoconference by the user in the sterile space, wherein the confirming initiates the videoconference and wherein the initiation prevents the reading and processing of optically readable representations by the user in the sterile space without prior approval of the remote user;

the initiation of the videoconference by the user in the sterile environment;

wherein the remote users in the videoconference are shown via their screen a graphical presentation comprising several sections, wherein each of the remote users in the videoconference, the user in the sterile environment and the imaging instruments to be visualized are visualized separately in one of the sections, and wherein sections associated with one of the imaging instruments to be visualized display at least the visual output of said instrument;

wherein the remote users who have joined the videoconference gain control over the shared visual output, the control comprising at least manipulating focus and contrast of the shared visual output, visually perceivably annotating the shared visual output in the videoconference.

2. The method according to claim 1, wherein the image sensor of the user in the sterile environment is integrated in a hands-free device comprising a display, wherein the user in the sterile environment is shown said graphical presentation via the display.

3. The method according to claim 1, wherein the image sensor of the user in the sterile room can be controlled by the remote users in the videoconference, and wherein visual output of said image sensor is displayed in the graphical presentation.

4. The method according to claim 1, wherein the visual output of at least one of the imaging instruments is a video feed.

5. The method according to claim 1, wherein the remote user can select a section of the graphical presentation as focus, wherein the visual output of the selected section is magnified in the graphical presentation.

6. The method according to claim 5, wherein the method comprises an automated step of periodically adjusting a resolution at which the magnified visual output of the selected imaging instrument is displayed on the remote users' screen, depending on at least the incoming bitrate of data transfer from the selected imaging instrument.

7. The method according to claim 1, wherein the method comprises an automated step of periodically adjusting the resolution at which the visual output of one or more of the imaging instruments is shared via the videoconference, depending on at least the bitrate of data transfer over the connections of the display devices of the remote users.

8. The method according to claim 1, wherein the wearable image sensor of the user in the sterile environment comprises at least two mutually different image sensors, wherein at least one of the image sensors comprises a zoom lens, and the control by the remote users comprises varying the focal length of the zoom lens.

9. The method according to claim 1, wherein, between start-up and initiation of the videoconference, the user in the sterile environment is authorized to autonomously read in and process optically readable representations of one or more remote users to be invited, and/or to autonomously read in and process optically readable representations of one or more imaging instruments to be visualized from the instrument database;

wherein after the initiation of the videoconference, the reading in and processing of optically readable representations by the image sensor of the user in the sterile environment is disabled, and wherein after initiation, the reading in and processing of optically readable representations by the image sensor of the user in the sterile environment can be turned on by one of the remote users who joined the videoconference.

10. The method according to claim 1, wherein the remote users can provide additional visual output on the graphical presentation.

11. The method according to claim 1, wherein the instruments whose output is shared in the videoconference share the output via a wireless connection.

12. The method according to claim 1, wherein the instrument database further comprises a plurality of non-visual output-generating instruments and a separate, optically readable representation for each of the non-visual output-generating instruments, the method further comprising the following step:

reading in and processing with the image sensor the optically readable representations of one or more non-visual output-generating instruments to be visualized from the instrument database, wherein the non-visual output of the one or more non-visual output-generating instruments to be shared is shared during the video-conference in a section associated with the non-visual output-generating instrument.

13. The method according to claim 1, wherein the optically readable representation is provided on or at the imaging instrument.

14. The method according to claim 1, wherein one or more of the imaging instruments further generates non-visual output, the non-visual output being shared during the video conference.

15. The method according to claim 1, wherein an imaging instrument is provided in the sterile environment, which is configured to display the graphical presentation of the videoconference.

16. The method according to claim 1, wherein remote users may provide augmented reality content in the shared visual output for marking objects and/or zones in the visual output, wherein said augmented reality content is anchored to the marked object and/or zone, and wherein upon movement of the marked object and/or zone, the position of the augmented reality content is adjusted based on said movement.

17. The method according to claim 1, wherein the optically readable representation is a QR code.

18. The method according to claim 1, wherein the hands-free image sensor is provided on the user's head.

19. The method of claim 1, wherein the initiation of the videoconference by the user in the sterile environment is by reading in with the image sensor an optically readable representation provided in the sterile environment associated with the user in the sterile space.

20. The method according to claim 1, wherein the wearable, hands-free image sensor is on a pair of glasses.

* * * * *